(12) United States Patent
Esrock

(10) Patent No.: US 6,283,750 B1
(45) Date of Patent: Sep. 4, 2001

(54) METHOD OF CONNECTING A SYRINGE TIP TO A DENTAL SYRINGE HAND PIECE

(76) Inventor: Bernard S. Esrock, 896 Bluespring La., St. Louis, MO (US) 63131

( * ) Notice: Subject to any disclaimer, the term of this patent is extended or adjusted under 35 U.S.C. 154(b) by 0 days.

(21) Appl. No.: 09/580,706

(22) Filed: May 30, 2000

Related U.S. Application Data

(63) Continuation of application No. 09/400,217, filed on Sep. 21, 1999.

(51) Int. Cl.$^7$ .................................................. A61G 17/02
(52) U.S. Cl. ............................................................. 433/80
(58) Field of Search ............................... 433/80, 89, 126, 433/82; 604/77

(56) References Cited

U.S. PATENT DOCUMENTS

| | | |
|---|---|---|
| 3,698,088 | 10/1972 | Austin, Jr. . |
| 4,026,025 | 5/1977 | Hunt . |
| 4,133,564 | 1/1979 | Sarson et al. . |
| 4,149,315 | 4/1979 | Page, Jr. et al. . |
| 4,193,616 | 3/1980 | Sarson et al. . |
| 4,248,589 | 2/1981 | Lewis . |
| 4,508,369 | 4/1985 | Mode . |
| 4,621,842 | 11/1986 | Kowal et al. . |
| 4,712,813 | 12/1987 | Passerell et al. . |
| 4,807,911 | 2/1989 | Short . |
| 4,900,068 | 2/1990 | Law . |
| 4,975,054 | 12/1990 | Esrock . |
| 4,984,984 | 1/1991 | Esrock . |
| 5,048,872 | 9/1991 | Gehring . |
| 5,049,071 | 9/1991 | Davis et al. . |
| 5,125,835 | 6/1992 | Young . |
| 5,236,356 | 8/1993 | Davis et al. . |
| 5,242,300 | 9/1993 | Esrock . |
| 5,286,065 | 2/1994 | Austin et al. . |
| 5,306,146 | 4/1994 | Davis et al. . |
| 5,342,195 | 8/1994 | Davis et al. . |
| 5,370,423 | 12/1994 | Guest . |
| 5,433,485 | 7/1995 | Austin, Jr. et al. . |
| 5,460,619 | 10/1995 | Esrock . |
| 5,468,027 | 11/1995 | Guest . |
| 5,489,205 | 2/1996 | Davis et al. . |
| 5,507,537 | 4/1996 | Meisinger et al. . |
| 5,591,389 | 1/1997 | Esrock . |
| 5,772,433 | 6/1998 | Esrock . |
| 5,927,975 | 7/1999 | Esrock . |

OTHER PUBLICATIONS

Norgren publication entitled, "Norgren Series 12 Inch Push-In Tube Fittings" published 05/96.
Alkon publication entitled, "Alkon Series AQ Push-In Tube Fittings," published prior to 09/99.
Parker Hannifin publication entitled, "Parker Prestolok/Prestolok II Fittings," published prior to 09/99.

(List continued on next page.)

Primary Examiner—Todd E. Manahan
(74) Attorney, Agent, or Firm—Senniger, Powers, Leavitt & Roedel

(57) ABSTRACT

In combination, a syringe tip and a dental syringe fitting for releasably connecting the syringe tip to a hand piece for delivering a fluid to a mouth of a patient. The hand piece has a passageway for delivering the fluid to a discharge end of the hand piece. The tip includes an interior passage for transporting the fluid to the patient and an exterior surface having a circumferential groove extending around the exterior surface of the tip. The fitting includes a body adapted to attach to the hand piece adjacent the discharge end, the body having a central opening sized and shaped for receiving the tip. A gripping mechanism is mounted in the opening and has a plurality of locking fingers disposed around the opening adapted to releasably engage the groove when the tip is received in the opening thereby to secure the tip to the hand piece. A method for connecting and disconnecting the syringe tip from the hand piece is also disclosed.

4 Claims, 7 Drawing Sheets

OTHER PUBLICATIONS

Pisco Pneumatic Equipment publication entitled, "Pisco Pnuematic Equipment" published prior to 09/99.

Nycoil publication entitled,"Push–In Tube Fittings" published prior to 9/99.

SMC publication entitled, "SMC Inch–Size One–Touch Fittings Series KQ" published prior to 09/99.

Imperial Eastman publication entitled, "Omega Flo" published Prior to 9/99.

Camozzi Pneumatics publication entitled, "Pro Fit Super–Rapid Pro fit Fittings for Plastics Tube" published prior to 09/99.

Dana publication entitled, "Push Connect" published prior to 09/99.

Legris publication entitled, "Advantages LF3000 Push–to–Connect Fittings" published prior to 09/99.

METHOD OF CONNECTING A SYRINGE TIP TO A DENTAL SYRINGE HAND PIECE

CROSS-REFERENCE TO RELATED APPLICATIONS

This is a continuation application of co-pending application Ser. No. 09/400,217 filed Sep. 21, 1999, entitled, "FITTING FOR DENTAL SYRINGE", which is hereby incorporated by reference.

BACKGROUND OF THE INVENTION

This invention relates generally to dental syringes, and more particularly to a method of releasably connecting a syringe tip to a hand piece for delivering a fluid to a mouth of a patient.

Dental syringes are hand-held devices for discharging fluids, such as pressurized air and water, into a patient's mouth. Syringes typically have a hand piece for gripping by a hand of a dentist or dental assistant and a fitting adapted for receiving a detachable tube or tip. Such syringes are described in co-assigned U.S. patent application Ser. No. 08/787,243, filed Jan. 24, 1997, which is hereby incorporated by reference. Fluids are conveyed through the hand piece and the fitting to the tip which delivers the fluids to the patient's mouth. The tip must be securely held by the fitting to prevent it from being ejected into the patient's mouth, and it must be clean to avoid spreading disease. To ensure the tips are clean, dentists typically change tips after each patient.

Ideally, a dentist should be able to quickly and securely lock a new tip in place. Unfortunately, many syringes of the prior art do not provide this ability. For instance, some fittings hold the tip in place with ball bearings which engage a circumferential groove extending around the tip. To use these fittings, the dentist must first depress a collar to permit the ball bearings to move radially outwardly so the tip can be inserted, and thereafter allow the collar to return to a locking position wherein the ball bearings are moved inwardly to engage the groove and lock the tip in position. These steps require the dentist to use both hands and can be awkward. Further, if the collar has not properly returned to its locking position, the tip remains loose and may be ejected from the syringe, posing a potential safety hazard.

Other fittings hold the tip with elastomeric O-rings which engage the circumferential groove around the tip. Although these fittings grip a new tip automatically when it is inserted, they rely solely on friction and elasticity from the O-rings to oppose removal of the tip. Because the magnitude of the frictional force is relatively limited, the tip is subject to ejection from the fitting when exposed to a strong force. Further, O-rings degrade over time which can diminish their elasticity and ability to generate frictional force, making the fitting unreliable.

SUMMARY OF THE INVENTION

Among the several objects and features of the present invention may be noted the provision of a dental syringe fitting which automatically locks a syringe tip in place upon insertion into the fitting; the provision of such a fitting which precludes accidental ejection of the tip from the fitting; the provision of such a fitting which sealingly connects passageways in a hand piece to passageways in a tip; and the provision of such a fitting which accepts syringe tips of a variety of constructions including tips made of plastic or metal.

Briefly, apparatus of the present invention includes a combination of a syringe tip and a fitting for releasably connecting the syringe tip to a hand piece for delivering a fluid to a mouth of a patient. The hand piece has a passageway for delivering the fluid to a discharge end of the hand piece. The tip includes an interior passage for transporting the fluid to the patient and an exterior surface having a circumferential groove extending around the exterior surface of the tip. The fitting comprises a body adapted to attach to the hand piece adjacent the discharge end. The body has a central opening sized and shaped for receiving the tip. Further, the fitting comprises a gripping mechanism mounted in the opening and having a plurality of locking fingers disposed around the opening adapted to releasably engage the groove when the tip is received in the opening thereby to secure the tip to the hand piece.

Another aspect of the present invention includes a dental syringe comprising a syringe tip having an exterior surface including a groove extending around the exterior surface of the tip. The syringe also includes a fitting having a central opening sized and shaped for receiving the syringe tip and a gripping mechanism mounted in the opening. The gripping mechanism has a plurality of locking fingers disposed around the opening adapted to engage the groove in the tip. Further, the syringe includes a hand piece having a discharge end and a socket generally at the discharge end for attaching the fitting to the hand piece.

In yet another aspect, the present invention includes a method of connecting a syringe tip to a dental syringe hand piece for transporting fluid to a patient. The method comprises the step of pushing the syringe tip through an opening in a fitting until a plurality of locking fingers engage a groove in an exterior surface of the tip.

In still another aspect the present invention includes a method of connecting a syringe tip to a dental syringe hand piece comprising the steps of moving a release to a releasing position to move fingers in a fitting outward thereby disengaging the fingers from a groove in the tip. While the release is in the releasing position, the syringe tip is pushed through the opening until the plurality of locking fingers are aligned with the groove in the exterior surface of the tip. The release is moved to the locking position to engage the fingers with the groove.

In addition, the present invention includes a method of disconnecting a syringe tip from a dental syringe hand piece comprising the steps of moving the release to the releasing position to move the fingers outward thereby disengaging the fingers from the groove and withdrawing the syringe tip from the opening until the plurality of locking fingers becomes offset from the groove in the exterior surface of the tip.

Other objects and features of the present invention will be in part apparent and in part pointed out hereinafter.

BRIEF DESCRIPTION OF THE DRAWINGS

Corresponding reference characters indicate corresponding parts throughout the views of the drawings.

DETAILED DESCRIPTION OF THE PREFERRED EMBODIMENT

Figure 1:
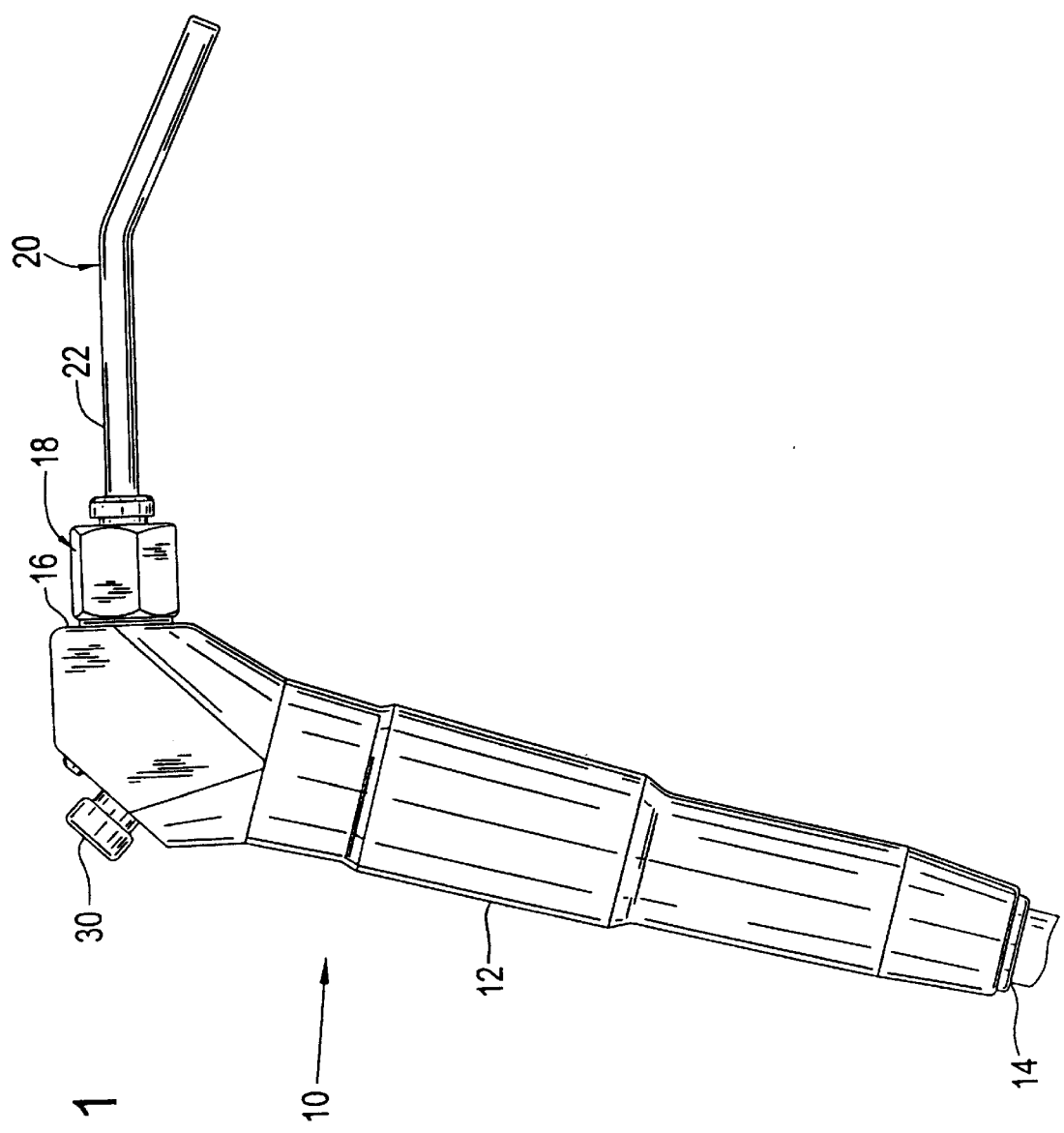
FIG. 1 is a side elevation of a dental syringe of the present invention.
Figure 2:
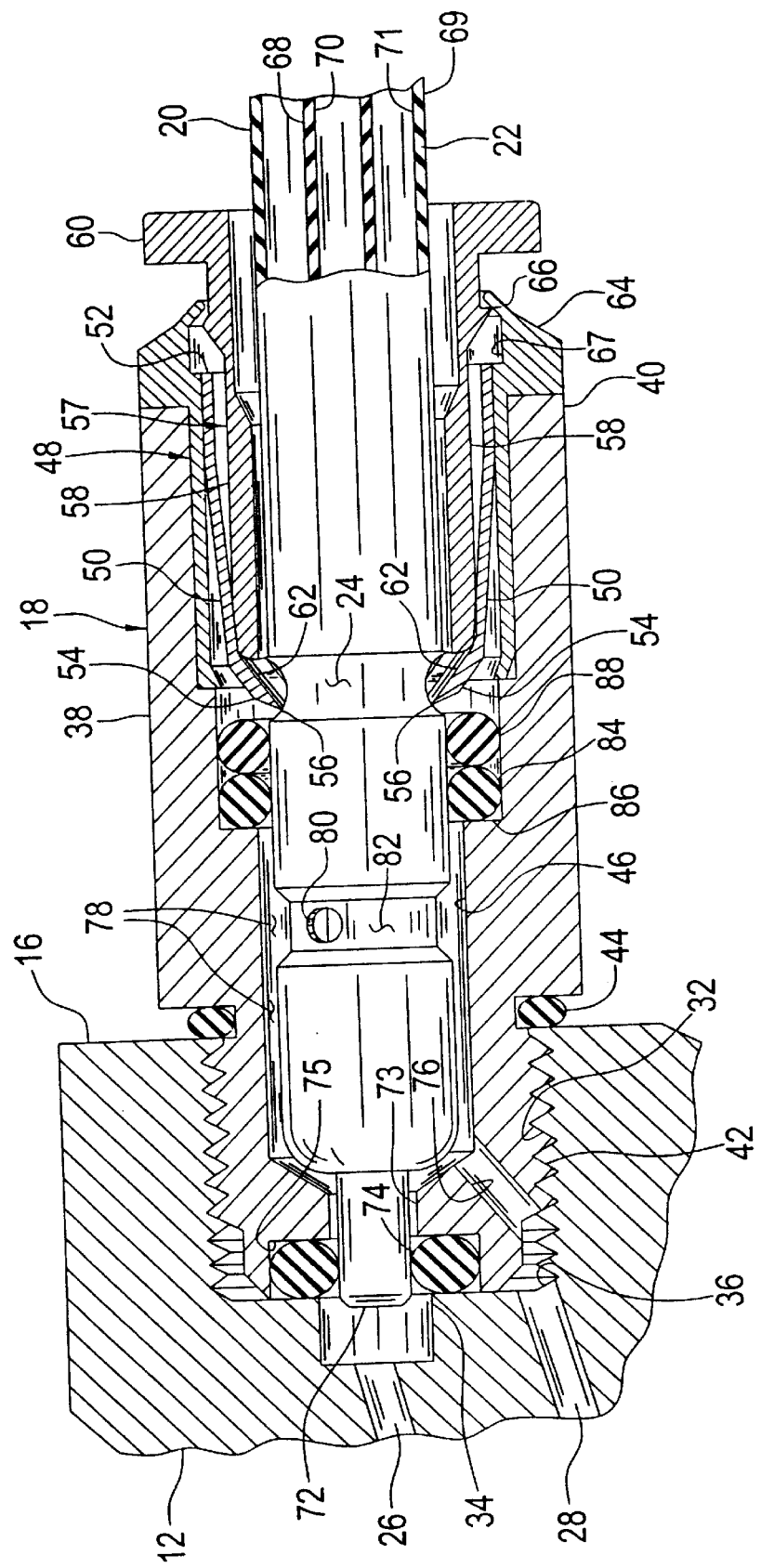
FIG. 2 is a partial vertical cross section of the syringe of FIG. 1 showing a gripping mechanism in a locking position.

Referring now to the drawings and in particular to FIG. 1, a dental syringe according to the present invention for delivering fluids to a mouth of a patient is indicated generally at 10. The syringe includes a conventional hand piece 12 shaped for gripping and having an intake end 14 and a discharge end 16. A fitting generally designated by 18 is attached to and extends from the hand piece 12 adjacent the discharge end 16. The fitting 18 is adapted for releasably connecting a tubular syringe tip 20 to the hand piece 12. The syringe tip 20 has a generally cylindrical exterior surface 22 and two interior passages (not shown) for transporting fluids to the patient. As illustrated in FIG. 2, a circumferential groove 24 extends around the exterior surface of the tip 20 for holding the tip in the fitting 18.

As illustrated in FIG. 2, the hand piece 12 includes two separate internal passageways 26, 28 for conveying two fluids, such as compressed air and water, from the intake end 14 to the discharge end 16. Two valves (not shown) control fluid flow through the passageways. Button controls 30 (only one control is visible in FIG. 1) are provided on the hand piece 12 for operating the valves. The hand piece 12 has an internally threaded socket 32 at the discharge end 16 where both of the internal passageways 26, 28 terminate. The first passageway 26, typically for water, terminates in a central region 34 of the socket. The second passageway 28, typically for pressurized air, terminates generally toward an outer margin 36 of the socket. Because the hand piece 12 is conventional, it will not be described in further detail.

As shown in FIG. 2, the fitting 18 has a generally cylindrical body 38 having a forward end 40 and an externally threaded back end 42 for attaching the fitting to the socket 32 of the hand piece 12. In the preferred embodiment, the body 38 is of one piece construction. An elastomeric O-ring 44 circumferentially positioned around the body 38 near the threaded back end 42 prevents leakage from between the hand piece and the body. Although the body 38 of the fitting 18 of the preferred embodiment is cylindrical, it may have other shapes such as hexagonal without departing from the present invention.

The body 38 has a central opening 46 sized and shaped for receiving the syringe tip 20. The opening 46 is generally cylindrical and has a larger diameter than the syringe tip 20. Although the opening 46 may have other diameters without departing from the scope of the present invention, the opening of the preferred embodiment has a diameter of about 0.157 inch to receive tips 20 having a diameter of about 0.153 inch.

Figure 3:
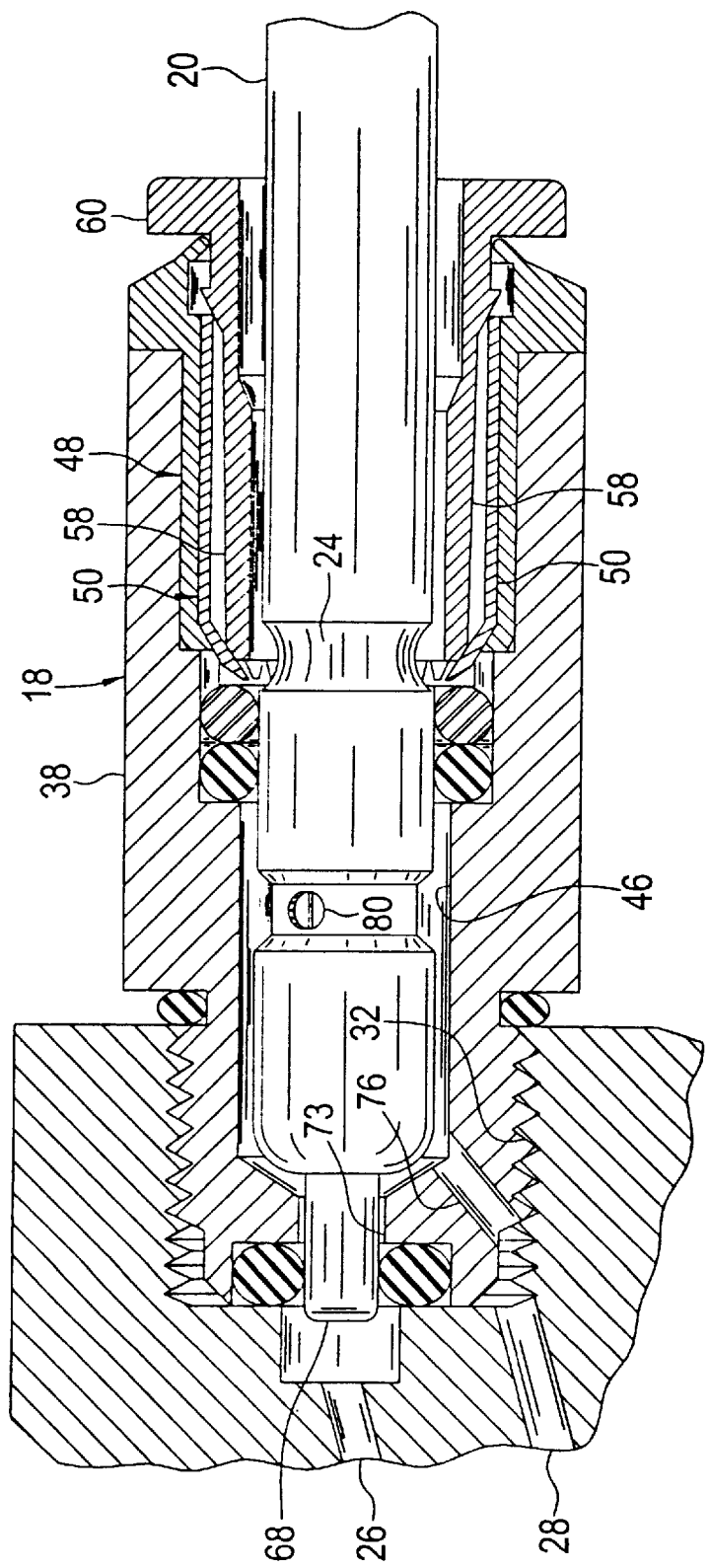
FIG. 3 is a view similar to that of FIG. 2 but showing the gripping mechanism in a releasing position.

A gripping mechanism, generally designated by 48, is mounted in the central opening 46 for gripping the syringe tip 20 and securing the tip to the fitting 18 and the hand piece 12. The gripping mechanism 48 includes a plurality of locking fingers 50 disposed around the opening 46 and adapted to releasably engage the circumferential groove 24 when the tip 20 is received in the opening. The locking fingers 50 are moveable between a locking position as shown in FIG. 2 in which the fingers engage the groove 24 to secure the tip 20 to the fitting 18 and a releasing position as shown in FIG. 3 in which the fingers disengage the groove to allow the tip to be removed from the fitting. The fingers 50 are resiliently biased radially inwardly toward the locking position. The gripping mechanism 48 is positioned in the body 38 at a location where its operation will not interfere with fluid connections of the two interior passages of the tip 20.

Figure 4:
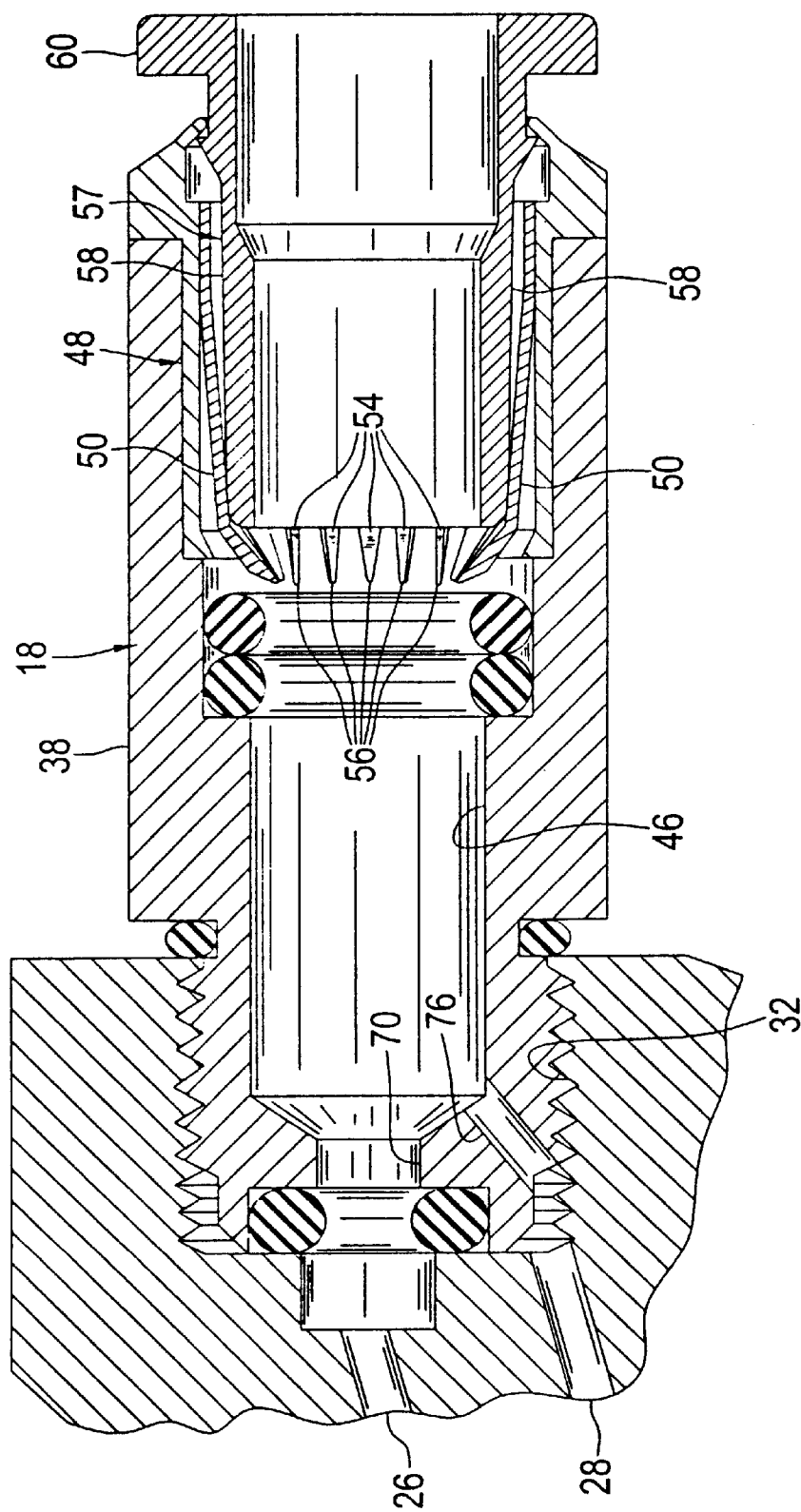
FIG. 4 is a view similar to that of FIG. 2 but showing a tip removed from the gripping mechanism.

Each of the locking fingers 50 extends rearwardly from a common retaining ring 52 located adjacent the forward end 40 of the body 38 to an inclined portion forming a tooth 54 extending radially inwardly at the rearward end of the finger. As shown in FIG. 4, each tooth 54 has a rearward facing edge 56 for engaging the groove 24. The teeth 54 of the locking fingers are positioned in the central opening 46 at an axial position that corresponds with an axial position of the groove 24 when the syringe tip 20 is received in the opening. Further, the teeth 54 are resiliently biased inwardly to a diameter less than a minimum diameter of the groove 24 to ensure positive engagement. Although the teeth 54 of the preferred embodiment are positioned at rearward ends of the locking fingers 50, it is envisioned that the teeth could be located at other positions along the locking fingers without departing from the scope of this invention.

A release, generally designated 57, is provided for moving the teeth 54 between the locking and releasing positions. The release comprises a collar 58 which is coaxially aligned with the opening 46 and positioned inside the locking fingers 50. The collar 58 has a flange 60 which protrudes from the forward end 40 of the body 38 for manually pushing the collar toward the hand piece 12. When the flange 60 is pushed rearward, the collar 58 moves toward the back end 42 of the body to the releasing position shown in FIG. 3 in which a rearward end of the collar engages a sloped surface 62 on each tooth 54 to push the teeth outwardly and disengage them from the groove 24.

The fingers 50 are resiliently biased inwardly, so that in the releasing position shown in FIG. 3, the surface 62 of the teeth press against the collar 58 to bias the collar toward the locking position. Thus, when not being manually pushed rearwardly, the collar 58 will automatically move to the locking position. The retaining ring 52 is attached to a housing 64 which surrounds the fingers 50 and collar 58. The housing 64 is press fit into the opening 46 of the fitting to hold the gripping mechanism 48 in position. A circumferential ridge 66 on the collar 58 is captured in a groove 67 in the housing 64 to prevent removal of the collar from the fitting 18.

The syringe tip 20 comprises two coaxially aligned tubes 68, 69 forming a first interior passage 70 for delivering the first fluid and a second interior passage 71 for delivering the second fluid. A portion of the first tube 68 extends from the rearward end of the tip 20 forming a longitudinal protrusion 72 extending from the tip having a smaller diameter than the tip. An orifice (not shown) on an end of the protrusion 72 permits fluid to enter the first interior passage from the socket 32 of the hand piece 12. The longitudinal protrusion 72 is received within a passage 73 that extends from the central opening 46 generally at the back end 42 of the body 38. The passage 73 is sized and shaped for receiving the protrusion 72. Although the passage 73 may have other diameters without departing from the scope of the present invention, the passage of the preferred embodiment has a diameter of about 0.068 inch to receive protrusions 72 having a diameter of about 0.062 inch. An elastomeric O-ring 74 is mounted against a shoulder 75 and disposed around the passage 73 for providing a fluid-tight sealing connection between the body 38 of the fitting, the protrusion 72, and the hand piece 12.

A passageway 76 extends through the back end 42 of the body 38 for delivering the second fluid from the discharge end 16 of the hand piece 12 at the outer margin 36 of the socket 32 to the central opening 46. In particular, the passageway 76 delivers the fluid through the body 38 to an annular passage 78 formed between the exterior surface 22 of the syringe tip 20 and the central opening 46. The tip 20 has an orifice 80 for delivering the second fluid from the annular passage 78 to the second interior passage 71. The orifice 80 shown in FIG. 2 is located on a second groove 82 that extends around the tip 20 on the exterior surface 22. However, it is understood that the orifice 80 may be located anywhere along the tip 20, including an end of the tip, and that the second groove 82 is not required. An elastomeric O-ring 84 is mounted in the opening 46 against a shoulder 86 and encircles the opening for providing a fluid-tight sealing connection between the body 38 of the fitting and the exterior surface 22 of the tip. Further, a second O-ring 88 is included in series with the first O-ring 84 as shown in FIG. 2 to improve the seal. The O-rings 84, 88 prevent the second fluid from leaking from the forward end of the central opening 46.

In operation, the fitting 18 automatically locks the syringe tip 20 in the opening 46 when the tip is inserted and prevents accidental ejection of the tip from the fitting. When the tip 20 is pushed into the opening 46, the locking fingers 50 of the gripping mechanism 48, which are biased toward the locking position, automatically engage the exterior surface 22 of the tip. As the tip 20 is pushed farther into the opening 46, the tip passes through the O-rings 84, 88 and the longitudinal protrusion 68 seats into the passage 73 at the back end 42 of the body 38. When fully inserted, the groove 24 of the tip 20 is positioned at an axial location corresponding to the teeth 54 of the locking fingers 50, thereby engaging the teeth with the groove and securing the tip in the fitting 18.

The tip 20 is positively locked in place against forces tending to remove it from the fitting 18, especially forces caused by fluid pressure and fluid flow which tend to eject the tip. Any movement of the tip 20 in a forward direction away from the hand piece 12 as to remove the tip from the opening 46 causes the teeth 54, which positively engage the groove 24, to bite into the groove. Due to the shapes of the rearward facing edges 56, the teeth 54 tend to grip the groove 24 and not move outward along the groove. A force applied on the tip 20 in a forward direction as to remove the tip from the opening is opposed by a corresponding holding force due to the teeth 54 engaging the groove 24. Therefore the tip 20 is positively locked in the fitting 18. Further, the teeth 54 bite into the groove 24 in part because of their geometries or shapes and not because any material properties. Thus, the fitting 18 may be used with tips 20 made from a variety of materials including plastic or metal.

Upon insertion of the tip 20 into the opening 46, the internal passageways 70, 71 within the tip are automatically and sealingly connected in fluid communication with the corresponding passageways 26, 28 in the hand piece 12. The syringe 10 is then ready for use in delivering one or both fluids from the hand piece 12 through the tip 20 to the mouth of the patient. When the dentist presses the first button control 30 to open the first valve, the first fluid is delivered from the intake end 14 of the hand piece 12 to the discharge end 16 at the central region 34 of the socket 32, thereafter through the orifice at the end of the longitudinal protrusion 68 and into the first interior passage 70 of the tip 20 and through the tip to the patient. When the dentist presses the second button control 30 to open the second valve, the second fluid is delivered from the intake end 14 of the hand piece 12 to the discharge end 16 at the outer margin 36 of the socket 32. The second fluid thereafter passes through the passageway 76 in the body 38 to the annular passage 78, through the orifice 80 into the second interior passage 71 of the tip and thereafter through the tip to the patient.

After use with the patient, the tip 20 is no longer clean and must be replaced. To remove the tip 20, the dentist applies force to the flange 60 of the release collar 58, thereby moving the collar rearward and pushing the teeth 54 of the locking fingers 50 outward to disengage the teeth from the groove 24. The tip 20 is pulled out of the opening 46 while applying the force to the flange 60.

Figure 5:
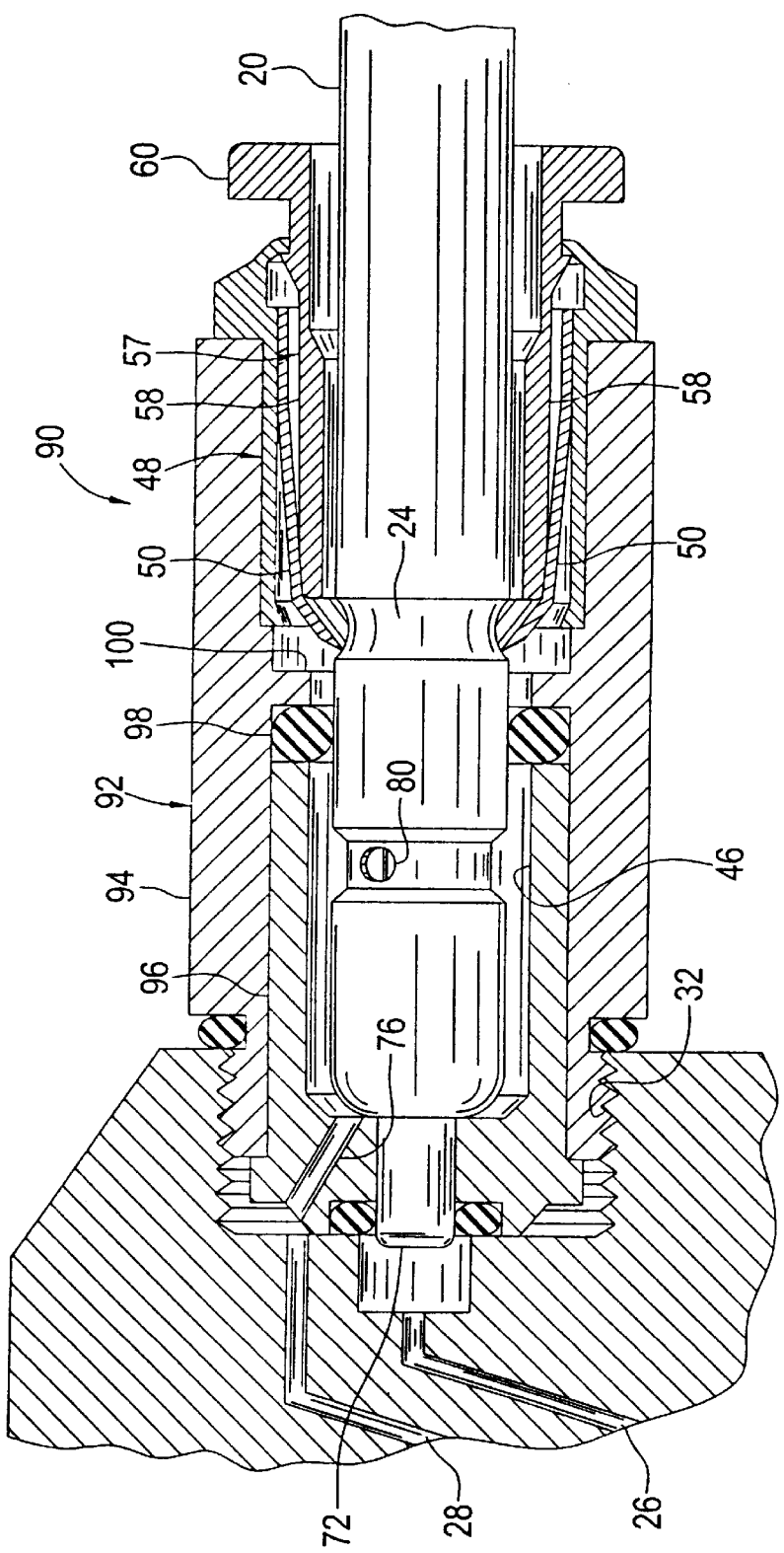
FIG. 5 is a partial vertical cross section of a second embodiment of the present invention.

A second embodiment 90 of the fitting 18 includes a body 92 constructed of two pieces, as shown in FIG. 5. The body 92 includes a generally cylindrical sleeve 94 and a cup-shaped insert 96. An elastomeric O-ring 98 is captured between the insert 96 and an internal circumferential ridge 100 on the sleeve 94. The O-ring 98 encircles the opening 46 for providing a fluid-tight sealing connection between the sleeve 94 and the exterior surface 22 of the tip 20. In other respects, the invention according to the second embodiment 90 shown in FIG. 5 is identical in structure and operation to the first embodiment shown in FIGS. 2–4.

Figure 6:
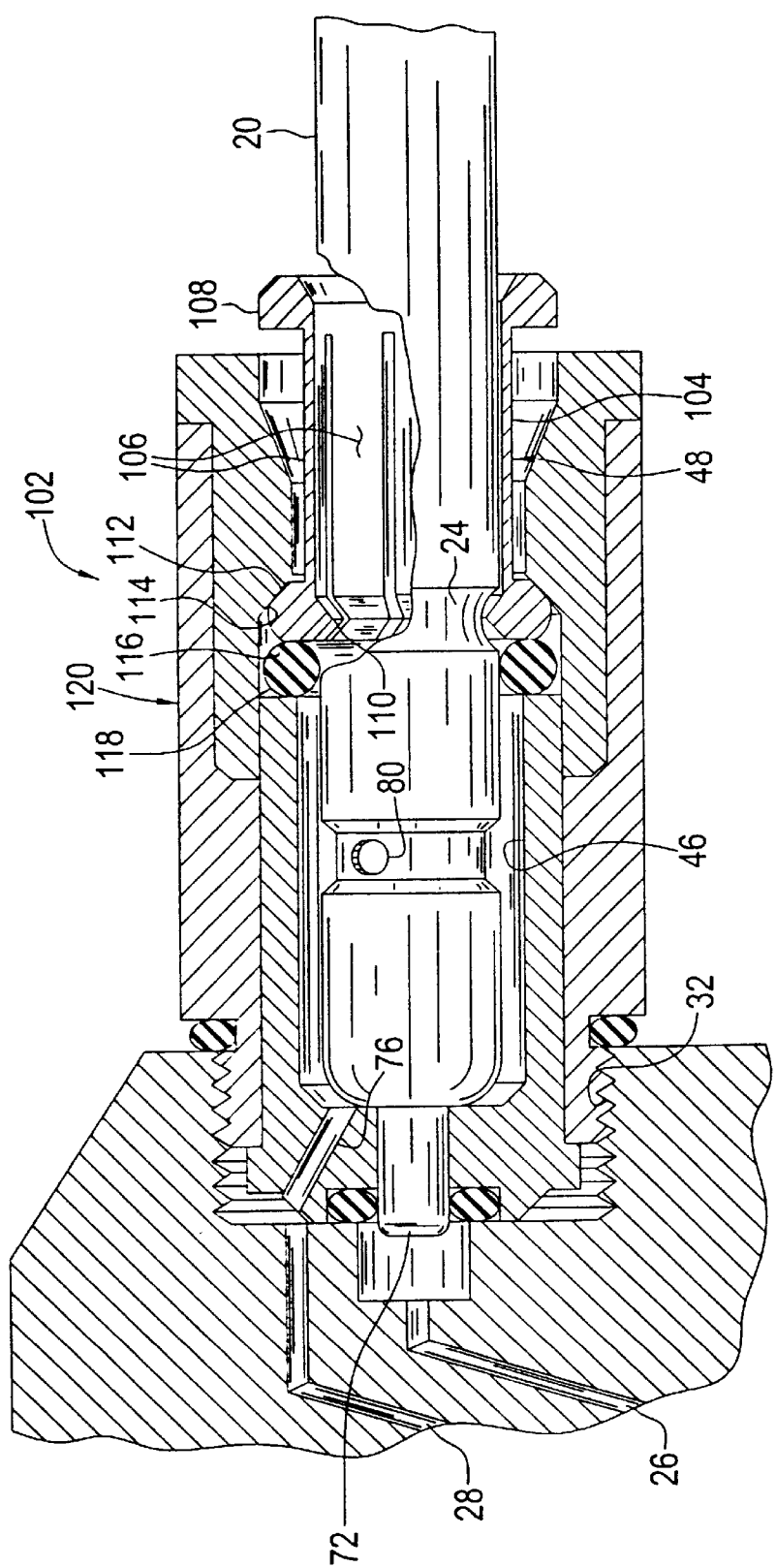
FIG. 6 is a partial vertical cross section of a third embodiment of the present invention.

A third embodiment 102 of the fitting 18 is shown in FIG. 6. Instead of a separate release collar and locking fingers, the gripping mechanism 48 of the third embodiment is a collet 104 having fingers 106 extending rearwardly from an integral flange 108. The fingers 106 of the collet 104 are resiliently biased radially outwardly. Each finger 106 has a tooth 110 which extends radially inwardly for engaging the groove 24 of the tip 20 and a forward-facing inclined surface 112 for engaging a rearward facing inclined shoulder 114 in the opening 46 of the body. The collet 104 is moveable between a locking position as shown in FIG. 6 in which the teeth 110 engage the groove 24 to secure the tip 20 to the fitting 18 and a releasing position (not shown) in which the teeth disengage the groove to allow the tip to be removed from the fitting. When the integral flange 108 is pushed rearwardly to move the collet 104 to the releasing position, the inclined surface 112 of the finger slides along the inclined shoulder 114 of the body to permit the fingers 106 to diverge radially outwardly and disengage the teeth 110 from the groove 24. A rearward facing end 116 of each finger 106 engages an elastomeric O-ring 118 captured in the opening 46 and disposed around the tip 20. The O-ring 118 biases the collet 104 forward so the inclined shoulder 114 causes the fingers 106 to deflect radially inwardly and engage the groove 24. The fitting of the third embodiment 102 includes a body 120 formed from three pieces. In other respects, the invention according to the third embodiment 102 of FIG. 6 is identical in structure and operation to the first embodiment of FIGS. 2–4.

Figure 7:
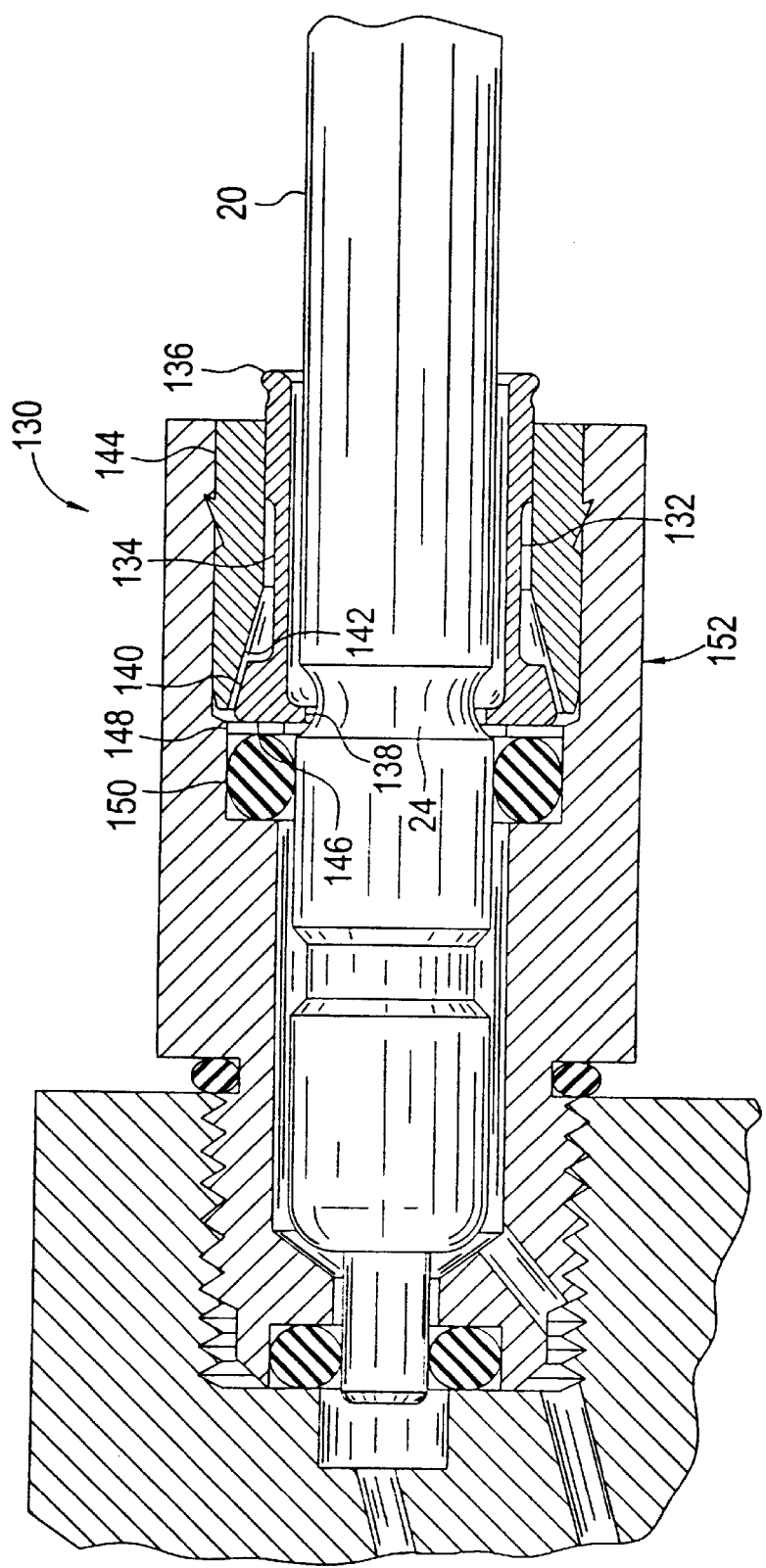
FIG. 7 is a partial vertical cross section of a fourth embodiment of the present invention.

A fourth embodiment 130 of the fitting 18 is shown in FIG. 7. The gripping mechanism 48 of the fourth embodiment is a collet 132 having fingers 134 extending rearwardly from an integral flange 136. The fingers are resiliently biased radially outwardly. Each finger 134 has a shoulder 138 which extends radially inwardly for engaging the groove 24 of the tip 20. Each finger 134 also has a forward-facing inclined surface 140 for engaging a rearward facing inclined shoulder 142 on a sleeve insert 144 in the opening 46 of the body. The collet 132 is moveable between a locking position as shown in FIG. 7 in which the shoulders 138 engage the groove 24 to secure the tip 20 to the fitting 18 and a releasing position (not shown) in which the shoulders disengage the groove to allow the tip to be removed from the fitting. When the integral flange 136 is pushed rearwardly to move the collet 132 to the releasing position, the inclined surface 140 of the finger slides along the inclined shoulder 142 of the sleeve insert 144 to permit the fingers 134 to deflect radially outwardly and disengage the shoulders 138 from the groove 24. A rearward facing end 146 of each finger 134 engages a spacer 148 in front of an elastomeric O-ring 150 captured in the opening 46 and disposed around the tip 20. The O-ring 150 biases the collet 132 forward toward the locking position, where the inclined shoulder 142 causes the fingers 134 to deflect radially inwardly and engage the groove 24. The fitting of the fourth embodiment 130 includes a body 152 formed from two pieces, including the sleeve insert 144. In other respects, the invention according to the fourth embodiment 130 of FIG. 7 is identical in structure and operation to the first embodiment of FIGS. 2–4.

Thus, the invention provides a dental syringe fitting which automatically locks the syringe tip in place upon insertion into the fitting, precludes accidental ejection of the tip, and simultaneously sealingly connects with two passageways in a hand piece for the delivery of two fluids.

In view of the above, it will be seen that the several objects of the invention are achieved and other advantageous results obtained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

What is claimed is:

1. A method of connecting a syringe tip to a dental syringe hand piece for transporting fluid to a patient, said syringe tip including an interior passage for transporting the fluid to the patient and an exterior surface having a circumferential groove extending around the exterior surface of the tip, said hand piece including a fitting having a central opening sized and shaped for receiving the tip and a gripping mechanism mounted in the opening, the mechanism having a plurality of locking fingers disposed around the opening adapted to releasably engage the groove when the tip is received in the opening thereby to secure the tip to the hand piece, said method comprising the step of pushing the syringe tip through the opening until the plurality of locking fingers engage the groove in the exterior surface of the tip.

2. A method of connecting a syringe tip to a dental syringe hand piece for transporting fluid to a patient, said syringe tip including an interior passage for transporting the fluid to the patient and an exterior surface having a circumferential groove extending around the exterior surface of the tip, said hand piece including a fitting having a central opening sized and shaped for receiving the tip and a gripping mechanism mounted in the opening, the mechanism having a plurality of locking fingers disposed around the opening adapted to releasably engage the groove when the tip is received in the opening thereby to secure the tip to the hand piece, and a release which is moveable between a locking position in which the fingers engage the groove to secure the tip to the fitting and a releasing position in which the fingers disengage the groove allowing the tip to be removed from the fitting, said method comprising the steps of:

moving the release to the releasing position to move the fingers outward thereby disengaging the fingers from the groove;

while the release is in the releasing position, pushing the syringe tip through the opening until the plurality of locking fingers are aligned with the groove in the exterior surface of the tip; and moving the release to the locking position to engage the fingers with the groove.

3. A method of disconnecting a syringe tip from a dental syringe hand piece for transporting fluid to a patient, said syringe tip including an interior passage for transporting the fluid to the patient and an exterior surface having a circumferential groove extending around the exterior surface of the tip, said hand piece including a fitting having a central opening sized and shaped for receiving the tip and a gripping mechanism mounted in the opening, the mechanism having a plurality of locking fingers disposed around the opening adapted to releasably engage the groove when the tip is received in the opening thereby to secure the tip to the hand piece, and a release which is moveable between a locking position in which the fingers engage the groove to secure the tip to the fitting and a releasing position in which the fingers disengage the groove allowing the tip to be removed from the fitting, said method comprising the steps of:

moving the release to the releasing position to move the fingers outward thereby disengaging the fingers from the groove; and while the release is in the releasing position, withdrawing the syringe tip from the opening until the plurality of locking fingers becomes offset from the groove in the exterior surface of the tip.

4. A method as set forth in claim 3 wherein the syringe tip is withdrawn completely from the opening while the release is in the releasing position.

* * * * *